United States Patent
Gouveris et al.

(10) Patent No.: US 12,303,691 B2
(45) Date of Patent: May 20, 2025

(54) DEVICE AND METHOD FOR DETERMINING SLEEP APNEA

(71) Applicant: Universitätsmedizin der Johannes Gutenberg-Universität Mainz, Mainz (DE)

(72) Inventors: Haralampos Gouveris, Mainz (DE); Muthuraman Muthuraman, Freimersheim (DE); Matthias Schwabe, Mainz (DE); Ali Abriani, Flensburg (DE); Philipp Tjarko Boekstegers, Mainz (DE); Sanja Mirjam Fassnacht, Mainz (DE); Elena Schmitt, Frankfurt am Main (DE); Katharina Bahr, Mainz (DE)

(73) Assignee: Universitätsmedizin der Johannes Gutenberg-Universität Mainz, Mainz (DE)

( * ) Notice: Subject to any disclaimer, the term of this patent is extended or adjusted under 35 U.S.C. 154(b) by 360 days.

(21) Appl. No.: 17/755,420

(22) PCT Filed: Oct. 29, 2020

(86) PCT No.: PCT/EP2020/080393
§ 371 (c)(1),
(2) Date: Apr. 28, 2022

(87) PCT Pub. No.: WO2021/084005
PCT Pub. Date: May 6, 2021

(65) Prior Publication Data
US 2022/0362553 A1    Nov. 17, 2022

(30) Foreign Application Priority Data
Oct. 30, 2019   (DE) .......................... 102019129288.3

(51) Int. Cl.
*A61N 1/00*   (2006.01)
*A61B 5/308*   (2021.01)
(Continued)

(52) U.S. Cl.
CPC ............ *A61N 1/3611* (2013.01); *A61B 5/308* (2021.01); *A61N 1/0551* (2013.01)

(58) Field of Classification Search
None
See application file for complete search history.

(56) References Cited

U.S. PATENT DOCUMENTS

2007/0239059 A1\* 10/2007 McIver .................. A61B 5/377
600/545
2014/0303459 A1\* 10/2014 Wada ................... A61B 5/1135
600/301
(Continued)

FOREIGN PATENT DOCUMENTS

EP   0199214        10/1986
EP   0199214 A2 \* 10/1986   ............. A61B 5/291
(Continued)

OTHER PUBLICATIONS

Varadan, V. et al., "Wearable technology and mobile platform for human health monitoring", Forum for Electromagnetic Research Methods and Application Technologies, Bd., Seiten 1-38, XP055765875, (Jul. 2016).

*Primary Examiner* — Sana Sahand
(74) *Attorney, Agent, or Firm* — McHale & Slavin, P.A.

(57) ABSTRACT

A device and method for determining the severity of sleep apnea using electroencephalography and electromyography. The device includes a headgear having a head part sized to cover the head of a patient, at least at the locations where the measuring points C3 and C4 of the electroencephalography are situated, and a chin part, and wherein the head part has two electrodes for sensing EEG-signals of the electroen-
(Continued)

cephalography at the electroencephalography points C3 and C4, and the chin part has at least one electrode for sensing the EMG-signal of the electromyography in the chin.

20 Claims, 4 Drawing Sheets

(51) Int. Cl.
*A61N 1/05* (2006.01)
*A61N 1/36* (2006.01)

(56) References Cited

U.S. PATENT DOCUMENTS

| | | |
|---|---|---|
| 2017/0087360 A1 | 3/2017 | Scheiner |
| 2018/0280694 A1* | 10/2018 | Mashiach ................ A61B 5/11 |

FOREIGN PATENT DOCUMENTS

| | | | |
|---|---|---|---|
| EP | 2767235 | 8/2014 | |
| WO | WO2012170816 | 12/2012 | |
| WO | WO-2012170816 A2 * | 12/2012 | ........... A61B 5/0476 |
| WO | WO2017201088 | 11/2017 | |

* cited by examiner

DEVICE AND METHOD FOR DETERMINING SLEEP APNEA

CROSS REFERENCE TO RELATED APPLICATIONS

This is a national stage filing in accordance with 35 U.S.C. § 371 of PCT/EP2020/080393, filed Oct. 29, 2020, which claims the benefit of the priority of German Patent Application No. 102019129288.3, filed Oct. 30, 2019, the contents of each are incorporated herein by reference.

TECHNICAL FIELD

The present invention relates to a device for determining sleep apnea, in particular a device for automatically determining sleep apnea and a method for determining sleep apnea using such a device.

PRIOR ART

Sleep apnea is a night-time breathing disorder in which there is repeated prolonged cessation of breathing or partial cessation of breathing. Prolonged cessation of breathing or prolonged partial cessation of breathing is defined as cessation of breathing or partial cessation of breathing lasting longer than 10 seconds. Brief pauses in breathing, lasting less than 10 seconds, are usually not considered harmful. However, if pauses in breathing or partial pauses in breathing occur more than live times per hour during sleep, this can have serious health consequences.

Sleep apnea or the severity of sleep apnea is usually determined in a sleep laboratory using cardiorespiratory polysomnography. The severity is currently divided into three severity groups.

With the known methods, breathing and respiratory events such as hypopneas (partial pauses in breathing) or apneas (complete pauses in breathing) are sensed during sleep using a respiratory flow sensor, two piezoelectric stretch belts around the chest and abdomen, and a pulse oximeter, which determines arterial oxygen saturation in the blood. Furthermore, brainwaves are recorded by means of electroencephalography (EEG) and eye movements by means of electrooculography (EOG). Finally, the muscle tone in the chin region is also monitored with adhesive electrodes attached to the chin.

Measurement of respiratory flow using a respiratory flow sensor is a nasal dynamic pressure measurement using a nasal cannula and/or a measurement of the oral respiratory flow using an oral thermistor.

A large number of electrodes arranged on the patient's head are necessary for determining brain waves by means of electroencephalography. Electroencephalography is used to differentiate between sleep and wake phases during the night (or during recording) to sense a sleep stage classification during the sleep phase and thus the sleep architecture as well as respiratory, motor, and physiological wake reactions, so-called arousals.

The large number of sensors used significantly disturbs the sleep of a test subject, so that the question arises as to whether the measured values obtained in the sleep laboratory are representative of sleeping in a home or familiar environment. For this reason, measurements are sometimes carried out on two consecutive nights.

Due to the large amount of measured data sensed, the evaluation of respiratory events itself takes a comparatively long time, even with automatic evaluation. Since previously known automated evaluations often do not work without errors, it is usually necessary for an expert to check the evaluation. This check, which in the worst case can be a complete visual evaluation, is very time-consuming. Reliable classification of the respiratory events of detected sleep apnea is therefore currently not possible without the help of an expert.

Because reliable determination of pauses in breathing or partial pauses in breathing due to sleep apnea is currently still very time-consuming, cessation of breathing or partial cessation of breathing due to sleep apnea is often diagnosed belatedly, so that people do not receive therapeutic help until very late.

Presentation of the Invention

It is therefore the object of the present invention to provide a device for automatically determining sleep apnea states in a person, which device disturbs the sleep of a patient less than previously known devices. In addition, the object of the present invention is to provide a method with which it is possible, in a simple manner, to reliably and automatically detect sleep apnea states and which is also able to determine the severity of sleep apnea that has been found.

Finally, it is the object of the present invention to provide a device and a method for treating cessation or partial cessation in breathing connected to sleep apnea.

The invention is based on the finding that coherence between electroencephalography signals and electromyography signals permits a statement about sleep apnea states, in particular about the severity of a sleep apnea.

In particular, the invention is based on the finding that the coherence of EEG signals at electroencephalography points C3 and C4 and of muscle tone at the chin permits the severity of sleep apnea in humans to be classified.

The inventive device for determining the severity of sleep apnea thus draws on electroencephalography (EEG) and electromyography (EMG), which can be used to determine muscle tone.

The device itself comprises headgear having a head part covering the head of a patient, at least at the locations where the measuring points C3 and C4 of the electroencephalography are, and a chin part, and wherein the head part has two electrodes for sensing EEG signals of the electroencephalography at the electroencephalography points C3 and C4, and the chin part has at least one electrode for sensing the EMG signal of the electromyography at the chin.

Because the present device only draws from the measurement signals of the electroencephalography and electromyography, it is possible for the device for determining sleep apnea to have significantly simpler configuration.

In particular, it is possible to do without the respiratory flow sensors. The previously necessary piezoelectric stretch belts about the chest and abdomen, as well as the pulse oximeter, which determines arterial oxygen saturation in the blood, are no longer necessary, either. It is understood that if sensing of the latter values is desired, the present device for determining sleep apnea can still be combined with these measuring devices.

The electrodes for sensing EEG signals and the at least one electrode for sensing the EMG signal are measuring electrodes. The number of measuring electrodes required for the electroencephalography has therefore been reduced to a minimum. In total, there are only three measuring electrodes, if necessary four, as indicated below that are necessary for performing a measurement to determine sleep apnea and the severity of a sleep apnea, specifically two electrodes for sensing EEG signals of the electroencephalography, preferably at electroencephalography points C3 and C4, and two electrodes for sensing the EMG signal of the electromyography on the chin.

The headgear, in which the head part and the chin part are integrally connected to one another, is comparatively easy to wear, so that the sleeping conditions during the examination are not much different from those under normal circumstances.

A reference electrode and a grounding electrode are preferably provided in order to reliably and correctly sense the EEG signals in connection with the electroencephalography. The headgear preferably also covers the points on the patient at which the reference electrode and ground electrode are used on the patient.

In one preferred embodiment, at least one electrode is securely integrated into the headgear, so that the at least one electrode does not accidentally detach from the cap during the night-time examination. It is understood that all of the electrodes can be securely integrated into the headgear to ensure that no electrodes accidentally detach during sleep.

It has been found that sleep apnea can be ascertained particularly well if two electrodes are provided for sensing the EMG signal, each of which electrodes senses the muscle tone on the chin on the right and left side of a patient's face. For this reason, it is advantageous for the headgear to have a first half, a second half, and a longitudinal axis separating the first and second halves from one another, wherein two electrodes for sensing the EMG signal are provided and one is arranged on each half of the headgear. In one preferred refinement, the two electrodes are arranged symmetrical to the longitudinal axis in order to obtain two comparable measurement signals.

In order to disturb a patient's sleep as little as possible due to measuring devices and peripheral equipment, it is advantageous for the electrode for sensing the EEG signal and/or the electrode for sensing the EMG signal to be a wireless electrode.

Furthermore, it has proven advantageous for the electrode for sensing the EMG signal to be an adhesive electrode. Providing an adhesive electrode has the advantage that the electrode is held particularly securely at the desired measuring point on the patient's chin during sleep.

In one preferred refinement, a data processing device is provided which automatically evaluates the EEG signals and the at least one EMG signal in order to detect respiratory events without a large expenditure of time.

It is of further advantage here that wireless communication is provided between the data processing device and the electrodes. The communication between the electrodes, which sense the measurement data, and the data processing device, which evaluates the sensed measurement data, enables simple evaluation of the measurement data. With regular data transmission during the night-time measurement process, the data are thus already available for evaluation in the morning shortly after the end of the examination. Continuous transmission of the measurement data to a data processing device during the night-time examination even enables online observation of the patient. Providing wireless communication simplifies the structure of the measuring device, so that the patient's sleep is not affected or is only slightly affected by transmission of the data to a data transmission unit.

It is advantageous for the headgear to be designed like a cap and in particular to cover the back of the head essentially completely so that the device for determining sleep apnea does not slip out of place during sleep.

In order to hold the electrodes for determining muscle tone, in particular the electrodes for determining the EMG signal, securely at the desired measuring point, it is advantageous for the chin part to be designed as a chin strap.

As stated above, it is preferred that two EMG measuring electrodes are provided, each located on one half of the headgear. For this reason, it is useful for a first chin strap to be provided on the first half of the headgear and a second chin strap to be provided on the second half of the headgear.

Even if only one EMG measuring electrode is used on one half of the face, it is advantageous for a first chin strap to be provided on the first half of the headgear and a second chin strap to be provided on the second half of the headgear, since it is then possible in both cases to stably attach the chin straps to the patient's chin by connecting the first and second chin straps to one another. For example, the two chin straps can be connected by means of a belt or simply knotted using cords attached to the chin straps. Known alternative connection options such as hook-and-loop fasteners can also be used.

In one preferred refinement of the device for determining sleep apnea, means for stimulating breathing are provided. Thus, the device for determining sleep apnea not only determines sleep apnea, in particular determines the severity of sleep apnea, but is also a therapy device.

A device for determining sleep apnea in which the means for stimulating respiration comprise at least one implantable stimulation electrode, a data processing device for evaluating the EEG and/or EMG signals, a control unit, and a device for exciting the stimulation electrodes has proven to be a particularly effective and compact therapy device.

In order to be able to excite an implanted stimulation electrode, it is advantageous for the implanted stimulation electrode and the device for stimulating the stimulation electrode to each have a magnetic coil, wherein the coil of the device for stimulating the stimulation electrode is preferably connected to a battery or rechargeable battery. If the coil of the device for exciting the stimulation electrode is connected to a battery or rechargeable battery, the implanted stimulation electrode is supplied with power from the outside. It is thus easy to charge or change the battery.

The present invention also includes a method for determining sleep apnea by means of an inventive device and comprises the following steps:

Sensing the electrical activity of the brain by means of electroencephalography, wherein the EEG measurement signals sensed by means of electroencephalography are the measurement signals at the electroencephalography points C3 and C4;

Sensing the electrical muscle activity by means of electromyography, wherein the EMG measurement signal sensed by means of electromyography is a measurement signal in the region of the chin;

Correlating the EEG measurement signals sensed at points C3 and C4 and the EMG signal sensed in the region of the chin;

Evaluating the correlated EEG measurement signals at locations C3 and C4 and the EMG signal in the region of the chin for the occurrence of sleep apnea-associated respiratory events.

In one preferred refinement, the sensed EEG measurement signals at points C3 and C4 and the sensed EMG signal in the region of the chin are correlated and the correlated EEG measurement signals at points C3 and C4 and the EMG signal in the region of the chin are evaluated automatically for the occurrence of sleep apnea-associated respiratory events.

Not only can the presence of sleep apnea be determined using the methods described, but also the severity of sleep apnea.

In one preferred refinement of the method described, the EEG signals at the points C3 and C4 and the EMG signals in the region of the chin are correlated and evaluated immediately after these signals are sensed. The evaluated data are transmitted to a control unit immediately after the evaluation. Depending on the evaluated data received, the control unit transmits control signals to a device for exciting implanted stimulation electrodes.

This method, in which the implanted stimulation electrodes are excited while a pause in breathing is sensed, is suitable not only for determining sleep apnea states, but also for treating patients with sleep apnea. Determining sleep apnea states and providing therapy to a patient with sleep apnea can be carried out at the same time, which brings considerable advantages for the patient.

The signal can be transmitted by radio, inductively, or capacitively from the device for exciting implanted stimulation electrodes to the implanted stimulation electrodes. The use of excitation coils is preferred.

It is possible to excite the stimulation electrodes with every breathing cycle, so that it is always certain that the patient does not have any pauses in breathing. However, it has been found that this method has the disadvantage that it requires a great deal of electrical energy, since the stimulation electrodes must be supplied with a comparatively large amount of energy essentially continuously. In one preferred refinement, the control unit only transmits control signals to the device for exciting implanted stimulation electrodes if the data received from the data processing device represent the state of apnea, whether complete cessation of breathing or a partial pause in breathing. Thus, it is possible to reduce significantly the energy consumption for therapy for sleep apnea.

BRIEF DESCRIPTION OF THE DRAWINGS

Preferred embodiments of the present invention are explained using the accompanying drawings, in which.

BEST WAY TO CARRY OUT THE INVENTION AND INDUSTRIAL APPLICABILITY

Figure 1:
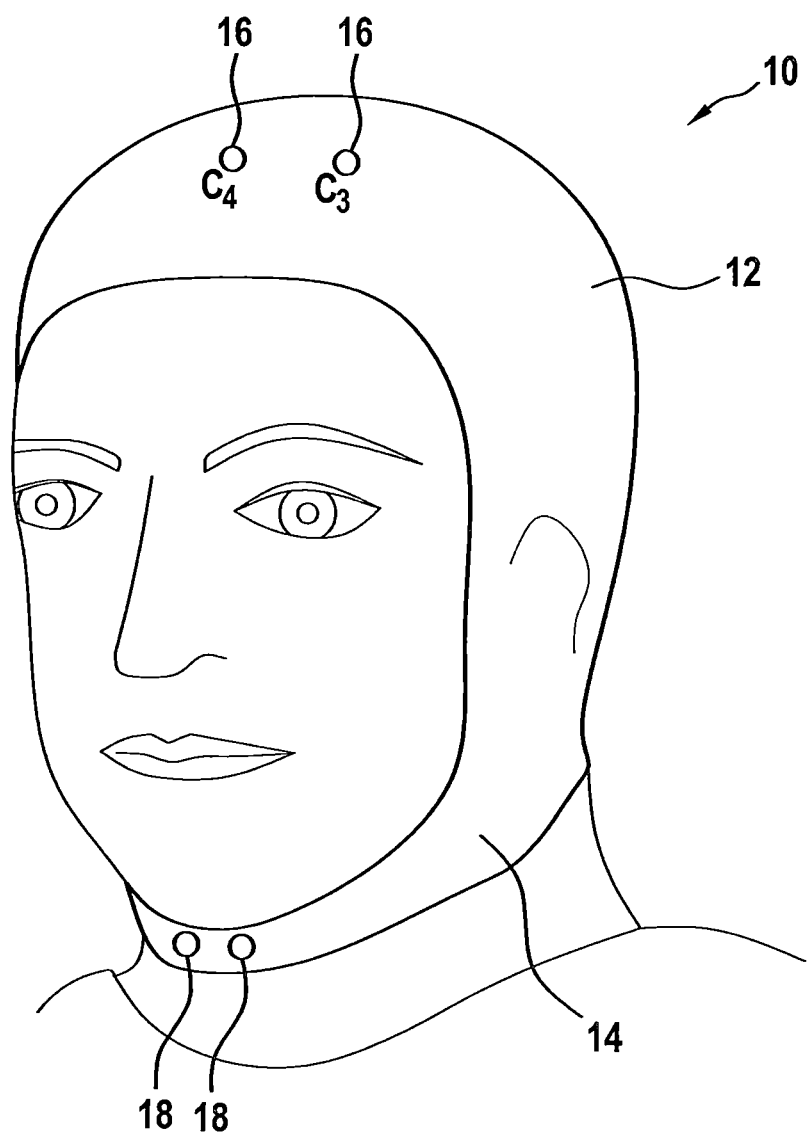
FIG. 1 depicts a first embodiment of a device for determining the severity of sleep apnea, which device is worn by a patient.

FIG. 1 depicts headgear 10 of a first embodiment of a device for determining the severity of sleep apnea by means of electroencephalography and electromyography. The headgear 10 includes only four measuring points at which patient-related measurement data are sensed, wherein there are two measuring points for recording patient-related measurement data with electroencephalography and the other two measuring points are for recording patient-related measurement data in connection with electromyography.

Patient-related measurement data are measurement data that are used to determine sleep apnea states.

The headgear comprises a head part 12 and a chin part 14. The head part 12 and chin part 14 are connected to one another, so that the headgear is embodied in one piece.

The head part 12 fits snugly against a patient's head and completely covers the upper head region and the side head region of a patient. Although not shown, the head part can also extend over the back of the patient's head.

In order to be comfortable to wear, the headgear comprises a textile material or a comparable flexible material.

Electrodes 16 for sensing an electroencephalography signal (EEG signal) are provided on the head part 12 at the positions that correspond to the electroencephalography points C3 and C4 when the patient is wearing the headgear. These electrodes are used to sense patient-related measurement data and are therefore measurement electrodes.

The electrodes 16 for recording an EEG signal are wireless electrodes that forward data to a data processing device (not shown) via a radio link. The electrodes 16 for sensing an EEG signal are securely connected to the head part 12.

Although not shown, in addition to the electrodes 16 for sensing an electroencephalography signal (EEG signal), which are embodied as measuring electrodes, a grounding electrode and a reference electrode are provided and are securely connected to the head part 12. The grounding electrode and the reference electrode are useful in the context of electroencephalography in order to obtain correct measurement signals, in particular absolute measurement signals, not just relative measurement signals, from the measurement electrodes. The grounding electrode and the reference electrode are therefore not used for recording patient-related measurement data, but instead are used to ensure the quality of the signals sensed by means of the electrodes 16 for recording an EEG signal.

Two electrodes 18 for sensing an electromyography signal (EMG signal) are provided in the region of the chin, symmetrical to the axis of the face. The two electrodes 18 for sensing the EMG signal are integrated in the chin part 14 of the headgear 10 and are therefore securely connected to the headgear 10. The two electrodes 18 for sensing the EMG signal are adhesive electrodes that, like the electrodes 16 for sensing an EEG signal, wirelessly transmit data to a data processing device (not shown).

The chin part 14 is embodied as a chin strap and is connected in one piece to the head part 12, so that the headgear 10 is embodied like a balaclava.

In one embodiment (not shown), the chin strap can have two chin straps, each of which is attached to one half of the head part 12. The two free ends of the chin strap can be firmly connected to one another by means of a belt, a buckle, or simply by means of cords.

Thus, to determine the severity of sleep apnea, the EEG signals are sensed at the C3 and C4 sites during sleep. Furthermore, during the night-time examination, the signals of the muscle tone on the chin are registered in the form of EMG signals using electromyography. The sensed measurement data are transmitted at regular intervals by radio to a data processing device (not shown). There they are evaluated for the occurrence of respiratory events. This can be done online during the night-time measurement process or offline after the end of the sleep. Both a visual evaluation by an expert and an automatic evaluation using a software program are possible.

In particular, the evaluation is carried out by correlating the EEG signals at the C3 and C4 points and the EMG signals sensed at the patient's chin.

The EEG/EMG signal combination in healthy people differs significantly from the EEG/EMG signal combination sensed in patients suffering from hypopnea or apnea. It is thus possible to classify the severity of an apnea using the EEG/EMG signal combination.

Since the number of measured values sensed in the method described is significantly reduced compared to conventional methods for classifying the severity of apnea, the evaluation is significantly faster and simpler without an increase in susceptibility to errors.

In the case of the headgear depicted for the device for determining the severity of sleep apnea, headgear was selected in which the head part essentially completely covers the head. Within the scope of the invention, however, it is sufficient for the head part of the headgear to cover the points required for measuring the C3 and C4 signal of the electroencephalography. However, it should be ensured that the headgear does not shift during the examination, i.e., during sleep.

The device described for determining the severity of sleep apnea has a comparatively simple structure and can therefore be produced inexpensively. The secure integration of the measuring electrodes in cap-like or hat-like headgear means that the patient's sleep is hardly affected during the night-time examination, so that measurement results are obtained that very likely have been sensed even during undisturbed sleep. The simple structure of the device described even makes it possible to use the device in a domestic environment, so that the measurement data sensed reflect the actual sleep situation at home to the greatest extent possible.

Figure 2:
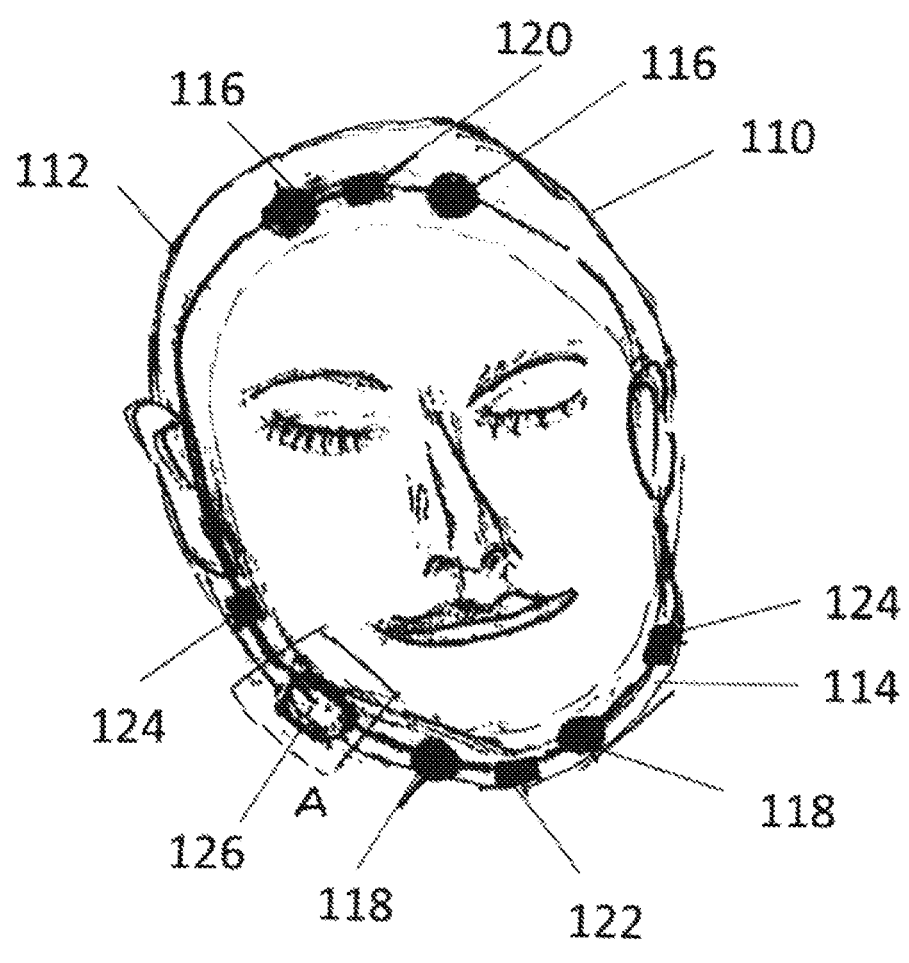
FIG. 2 depicts a second embodiment of a device for determining the severity of sleep apnea, which device is worn by a patient and which is also suitable for controlling muscle functions.
Figure 3:
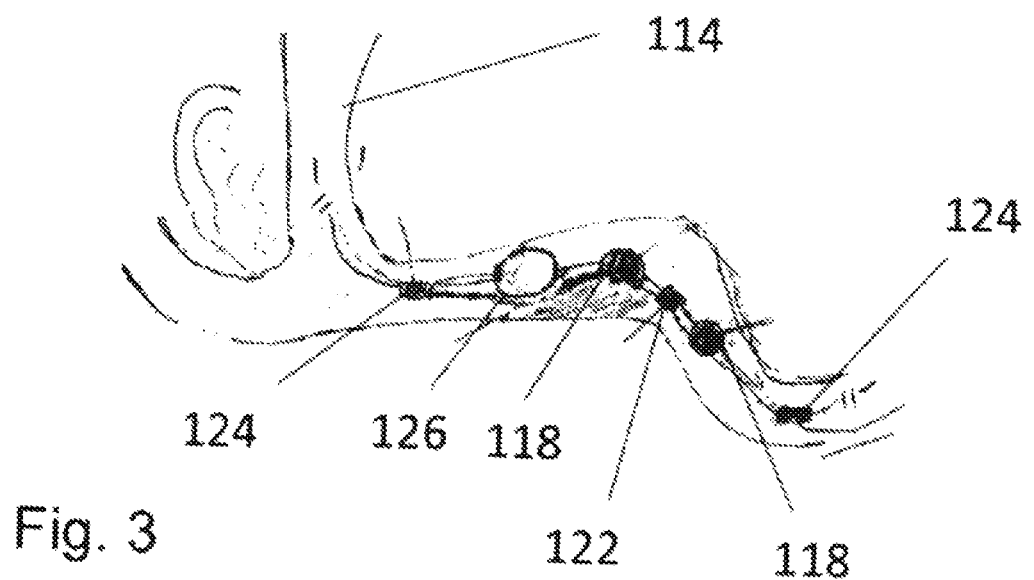
FIG. 3 depicts a detail from the embodiment shown in FIG. 2.
Figure 4:
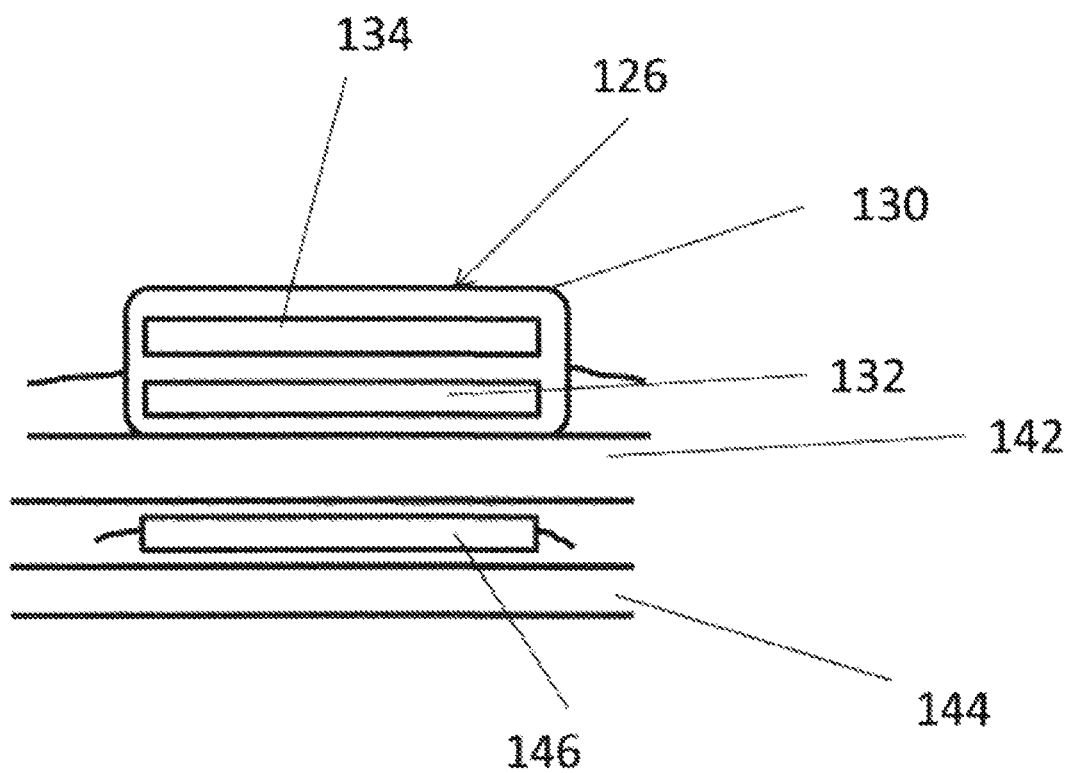
FIG. 4 depicts a section through a device for exciting the stimulation electrodes.

A second embodiment of a device for determining the severity of sleep apnea, which device is worn by a patient, is shown in FIGS. 2 to 4. It is also possible to control muscle functions and/or nerve functions, and thus to treat cessation of breathing or partial pauses in breathing using this second embodiment.

Like the headgear 10 depicted in FIG. 1, the headgear depicted in FIGS. 2 to 4 comprises a head part 112 and a chin part 114. Head part 112 and chin part 114 are connected to one another, so that headgear 110 is embodied in one piece. Furthermore, electrodes 116 for sensing an electroencephalography signal (EEG signal) are provided on the head part 112 at the positions that, when worn by the patient, correspond to the electroencephalography points C3 and C4. Two electrodes 118 for sensing an electromyography signal (EMG signal) are provided in the region of the chin symmetrical to the axis of the face.

In addition to the embodiment depicted in FIG. 1, the headgear 110 comprises a first amplifier 120, which amplifies the measurement signals of the electroencephalographic (EEG) signals and is attached between the two electroencephalography points C3 and C4.

A second amplifier 122 is provided between the two electrodes for sensing the electromyography signal 118.

Furthermore, a microprocessor 124 is arranged on each half of the face between the respective electrodes 116 for sensing an electroencephalography signal (EEG signal) and electrodes 118 for detecting an electromyography signal (EMG signal). The microprocessor 124 houses a data processing device and a control unit.

A device for exciting a stimulation electrode 126 is provided on one half of the face below the edge of the lower jaw.

The first and second amplifiers 120, 122, the microprocessors 124, and the device for exciting a stimulation electrode 126 are each securely connected to the headgear 110.

The electrodes 116 for detecting an electroencephalography (EEG) signal, the electrodes 118 for detecting an electromyography (EMG) signal, the first and second amplifiers 120, 122, the microprocessors 124, and the device for exciting a stimulation electrode 126 are connected to one another via a cable connection. Alternatively, the aforesaid parts can communicate entirely or in part by radio.

As shown in FIG. 4, the device for exciting stimulation electrodes 126 comprises a cover 130 that is integrated into the headgear 110 and in which are arranged a coil 132 and a battery 134.

The magnetic induction coil 146, which is in communication with an implanted stimulation electrode, is implanted either between subcutaneous tissue 142 and platysmal muscle layer 144 (as in FIG. 4) or beneath platysmal muscle layer 144 (not shown). The implanted stimulation electrode encloses the respective nerve. It is, for example, a so-called cuff electrode.

The battery 134 or the rechargeable battery is exchangeably arranged in the cover 130 of the device for exciting implanted stimulation electrodes 126, so that the implanted stimulation electrode can be supplied with energy from the outside. This offers significant advantages for the patient.

The precise position of the device for exciting the stimulation electrode 126 is thus selected such that it is arranged on the subcutaneously implanted coil 146, which is in communication with a patient's implanted stimulation electrode.

The two electrodes for sensing the EEG signals 116 and the two electrodes for sensing the EMG signals 118, the two amplifiers 120, 122, the two microprocessors 124, and the device for exciting implanted stimulation electrodes 126 communicate as follows:

The signals sensed by the two electrodes for sensing EEG signals 116 and the two electrodes for sensing EMG signals 118 are amplified and transmitted to the microprocessors 124 by means of the respective amplifiers 120, 122. In the microprocessor 124, the EEG signals and EMG signals are evaluated for the presence of sleep apnea states. The control unit contained in the microprocessor 124 transmits signals to the device for exciting implanted stimulation electrodes 126 to stimulate respiration, in particular to stimulate muscles involved in respiration. A stimulation signal is given to the muscle or nerve to stimulate respiration by means of the coil 132 in the device for exciting implanted stimulation electrodes 126 and the coil 146, which is connected to the stimulation electrode.

The control unit preferably only sends signals to the device for exciting implanted stimulation electrodes 126 when the EEG or EMG signal data sensed by the microprocessor 124 have sensed a pause in breathing in the form of sleep apnea or sleep hypopnea. Alternatively, the device for exciting implanted stimulation electrodes 126 can deliver a signal to the implanted stimulation electrode only when there is sleep apnea or hypopnea.

For example, the values of the EEG-EMG coherence are determined every 5-10 seconds in real-time by means of an adaptive closed-loop system, and these data are then used for stimulating breathing in the respiratory cycle during sleep during the next 5-10 seconds.

Although the invention has also been described in connection with a stimulation electrode in the mouth region, it is also possible to position the device for exciting implanted stimulation electrodes at other locations. The device for exciting implanted stimulation electrodes is preferably arranged in the headgear such that, when worn by the patient, it is positioned against the implanted stimulation electrode. The implanted electrodes can excite both muscles and nerves.

The data sensed and transmitted by the microprocessor can be stored and made available for later evaluation, for example by medical personnel. It is understood that the sensed and transmitted data can also be evaluated online or directly following the measurement.

Although not shown, the stimulation electrodes can also be excited in a different manner known in the prior art.

It is understood that the embodiments described in connection with the figures can be combined with one another. Individual features described in the embodiments can also be omitted within the scope of the invention.

The invention claimed is:

1. A device for determining sleep apnea by means of electroencephalography and electromyography, comprising a headgear having a head part configured to cover a head of a patient at least at the locations where measuring points C3 and C4 of the electroencephalography are situated, and having a chin part, said head part and said chin part integrally formed as a single unit, wherein the head part has two electrodes for sensing EEG signals of the electroencephalography at the electroencephalography points C3 and C4, and the chin part has at least one electrode for sensing the EMG signal of the electromyography on the chin, wherein the headgear has a first half, a second half, and a longitudinal axis separating the first and second halves wherein two electrodes for sensing the BMG signal are provided, each of which is arranged on one half of the headgear.

2. The device according to claim 1, characterized in that a reference electrode and a grounding electrode are provided in connection with the electroencephalography.

3. The device according to claim 1, characterized in that at least one electrode is securely integrated into the headgear.

4. The device according to claim 1, characterized in that the electrode for detecting the EEG signal and/or the electrode for detecting the EMG signal is a wireless electrode.

5. The device according to claim 1, characterized in that the electrode for detecting the EMG signal is an adhesive electrode.

6. The device according to claim 1, characterized in that a data processing device is provided which automatically evaluates the EEG signals and the at least one EMG signal.

7. The device according to claim 6, characterized in that wireless communication is provided between the data processing device and the electrodes.

8. The device according to claim 1, characterized in that the headgear is constructed and arranged to cover one or more portions of the head.

9. The device according to claim 1, characterized in that the chin part is designed as a chin strap.

10. The device according to claim 1, characterized in that the headgear has a first half, a second half and a longitudinal axis separating the first and second halves from one another, a first chin strap is provided on the first half of the headgear, and a second chin strap is provided on the second half of the headgear, wherein the first and second chin strap can be connected to one another.

11. The device according to claim 1, further comprising a stimulating respiration system configured for stimulating respiration.

12. The device according to claim 11, characterized in that the stimulating respiration system comprises at least one implantable stimulation electrode, a data processing device for evaluating the EEG signals and/or EMG signals, a control unit, and an apparatus for exciting the at least one implantable stimulation electrode.

13. The device according to claim 12, characterized in that the at least one implantable stimulation electrode and the apparatus for exciting the at least one implantable stimulation electrode each have a magnetic coil.

14. A method for determining sleep apnea by means of a device according to claim 1, comprising the following steps:
sensing the electrical activity of the brain by means of electroencephalography, wherein the EEG measurement signals sensed by means of electroencephalography are the measurement signals at the electroencephalography points C3 and C4;
sensing the electrical muscle activity by means of electromyography, wherein the EMG measurement signal sensed by means of electromyography is a measurement signal in the region of the chin;
correlating the EEG signals sensed at the points C3 and C4 and the EMG signal sensed in the region of the chin;
evaluating the correlated EEG signals at the points C3 and C4 and the EMG signal in the region of the chin for the occurrence of sleep apnea-associated respiratory events.

15. The method according to claim 14, characterized in that the steps
correlating the EEG signals sensed at points C3 and C4 and the EMG signal sensed in the region of the chin, and
evaluating the correlated EEG signals at the points C3 and C4 and the EMG signal in the region of the chin for the occurrence of sleep apnea-associated respiratory events are carried out automatically by means of a data processing device.

16. The method according to claim 15, characterized in that
the evaluation of the correlated EEG signals at points C3 and C4 and of the EMG signal in the region of the chin takes place immediately after these signals have been sensed;
the evaluated data are transmitted to a control unit immediately after the evaluation;
the control unit, depending on the evaluated data received, transmits control signals to an apparatus for exciting implanted stimulation electrodes.

17. The method according to claim 16, characterized in that a signal is transmitted from the apparatus for exciting implanted stimulation electrodes to an implanted stimulation electrode by radio, inductively, or capacitively.

18. The method according to claim 16, characterized in that the control unit only transmits control signals to the apparatus for exciting implanted stimulation electrodes if the data received from the data processing device represent the state of apnea or hypopnea.

19. The device according to claim 1, wherein the two electrodes are arranged symmetrically to the longitudinal axis.

20. The device according to claim 8, wherein said headgear is constructed and arranged to completely cover the back of the head.

* * * * *